US012667466B2

(12) United States Patent
Courtney, Jr. et al.

(10) Patent No.: US 12,667,466 B2
(45) Date of Patent: Jun. 30, 2026

(54) OSTEOTOME EXTRACTOR

(71) Applicant: Howmedica Osteonics Corp., Mahwah, NJ (US)

(72) Inventors: Robert Courtney, Jr., Pierceton, IN (US); Jeffrey M. Ondria, Warsaw, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 453 days.

(21) Appl. No.: 17/651,930

(22) Filed: Feb. 22, 2022

(65) Prior Publication Data

US 2022/0218497 A1 Jul. 14, 2022

Related U.S. Application Data

(60) Continuation of application No. 16/249,720, filed on Jan. 16, 2019, now Pat. No. 11,278,428, which is a
(Continued)

(30) Foreign Application Priority Data

Aug. 10, 2011 (FR) ...................................... 1157282

(51) Int. Cl.
*A61F 2/46* (2006.01)
*A61B 17/16* (2006.01)
(Continued)

(52) U.S. Cl.
CPC ............ *A61F 2/4603* (2013.01); *A61B 17/16* (2013.01); *A61B 17/1637* (2013.01);
(Continued)

(58) Field of Classification Search
CPC ....... A61B 17/92; A61B 17/921; A61B 17/16; A61B 17/1604; A61B 17/1659;
(Continued)

(56) References Cited

U.S. PATENT DOCUMENTS

| | | | |
|---|---|---|---|
| 448,126 | A | 3/1891 | Craig |
| 1,065,456 | A | 6/1913 | Lowrey |

(Continued)

FOREIGN PATENT DOCUMENTS

| | | |
|---|---|---|
| CA | 211530 | 5/2022 |
| CN | 202051851 U | 11/2011 |

(Continued)

OTHER PUBLICATIONS

Barth, et al., "Is global humeral head offset related to intramedullary canal width? A computer tomography morphometric study," Journal of Experimental Orthopaedics, 2018, vol. 5, pp. 1-8.
(Continued)

*Primary Examiner* — Amy R Sipp
(74) *Attorney, Agent, or Firm* — DUANE MORRIS LLP

(57) ABSTRACT

A method for separating an implant from a bone, includes interfacing a tool with an implant including a flange, the flange including a proximal surface and a distal surface, the distal surface bearing on or facing the bone, the flange including an aperture defined through the flange; inserting an elongate element through the aperture from the proximal surface to the distal surface and into the bone; and partially separating a bonding interface between the implant and the bone using the elongate element.

12 Claims, 4 Drawing Sheets

Related U.S. Application Data continuation of application No. 15/046,295, filed on Feb. 17, 2016, now Pat. No. 10,213,243, which is a division of application No. 13/553,610, filed on Jul. 19, 2012, now Pat. No. 9,289,218.

(60) Provisional application No. 61/509,506, filed on Jul. 19, 2011.

(51) Int. Cl.
*A61B 17/88* (2006.01)
*A61F 2/30* (2006.01)

(52) U.S. Cl.
CPC ........ *A61B 17/8872* (2013.01); *A61F 2/4607* (2013.01); *A61F 2/4612* (2013.01); *A61F 2002/30426* (2013.01); *A61F 2002/4619* (2013.01)

(58) Field of Classification Search
CPC ............ A61B 17/1664; A61B 17/1666; A61B 17/1671; A61B 17/1684; A61F 2/4603; A61F 2/4609; A61F 2/4612; A61F 2002/4619; A61F 2002/462; A61F 2002/4641
See application file for complete search history.

(56) References Cited

U.S. PATENT DOCUMENTS

| | | | |
|---|---|---|---|
| 1,123,730 A | 1/1915 | Greenfield | |
| 2,444,099 A | 6/1948 | Hennessey, Jr. | |
| 2,886,081 A | 5/1959 | Cowley | |
| 3,523,395 A | 8/1970 | Rutter et al. | |
| 3,609,056 A | 9/1971 | Hougen | |
| 3,738,217 A | 6/1973 | Walker | |
| 4,042,980 A | 8/1977 | Swanson et al. | |
| 4,147,464 A | 4/1979 | Watson et al. | |
| 4,250,600 A | 2/1981 | Gunther | |
| 4,261,062 A | 4/1981 | Amstutz et al. | |
| 4,406,023 A | 9/1983 | Harris | |
| 4,550,450 A | 11/1985 | Kinnett | |
| 4,601,289 A | 7/1986 | Chiarizzio et al. | |
| 4,623,353 A | 11/1986 | Buechel et al. | |
| 4,632,111 A | 12/1986 | Roche | |
| 4,743,262 A | 5/1988 | Tronzo | |
| D296,714 S | 7/1988 | Averill et al. | |
| 4,865,605 A | 9/1989 | Dines et al. | |
| 4,883,491 A | 11/1989 | Mallory et al. | |
| 4,919,670 A | 4/1990 | Dale et al. | |
| 4,964,865 A | 10/1990 | Burkhead et al. | |
| 4,986,833 A | 1/1991 | Worland | |
| 5,026,373 A | 6/1991 | Ray et al. | |
| 5,032,132 A | 7/1991 | Matsen et al. | |
| 5,035,717 A | 7/1991 | Brooks | |
| 5,044,393 A * | 9/1991 | Jiles | F16L 55/124 |
| | | | 408/67 |
| 5,080,673 A | 1/1992 | Burkhead et al. | |
| 5,112,338 A | 5/1992 | Anspach, III | |
| 5,163,961 A | 11/1992 | Harwin | |
| 5,163,964 A | 11/1992 | Lazzeri et al. | |
| 5,171,277 A | 12/1992 | Roger | |
| 5,257,995 A | 11/1993 | Umber et al. | |
| 5,282,865 A | 2/1994 | Dong | |
| 5,358,526 A | 10/1994 | Tornier | |
| 5,383,938 A | 1/1995 | Rohr et al. | |
| 5,401,125 A * | 3/1995 | Sevack | B23B 51/04 |
| | | | 408/203.5 |
| 5,443,471 A | 8/1995 | Swajger | |
| 5,489,309 A | 2/1996 | Lackey et al. | |
| 5,489,310 A | 2/1996 | Mikhail | |
| 5,507,817 A | 4/1996 | Craig et al. | |
| 5,514,136 A | 5/1996 | Richelsoph | |
| 5,534,006 A | 7/1996 | Szabo et al. | |

| | | | |
|---|---|---|---|
| 5,540,697 A | 7/1996 | Rehmann et al. | |
| 5,658,290 A | 8/1997 | Lechot | |
| 5,681,134 A | 10/1997 | Ebert | |
| 5,702,486 A | 12/1997 | Craig et al. | |
| 5,720,750 A | 2/1998 | Koller et al. | |
| 5,723,018 A | 3/1998 | Cyprien et al. | |
| 5,776,194 A | 7/1998 | Mikol et al. | |
| 5,800,551 A | 9/1998 | Williamson et al. | |
| 5,810,524 A * | 9/1998 | Wirth, Jr. | B23B 51/04 |
| | | | 408/206 |
| 5,820,315 A | 10/1998 | Collard | |
| 5,830,215 A | 11/1998 | Incavo et al. | |
| 5,849,015 A | 12/1998 | Haywood et al. | |
| 5,904,688 A | 5/1999 | Gilbert et al. | |
| 5,954,727 A | 9/1999 | Collazo | |
| 5,976,148 A | 11/1999 | Charpenet et al. | |
| 6,045,582 A | 4/2000 | Prybyla | |
| 6,063,124 A | 5/2000 | Amstutz | |
| 6,099,214 A | 8/2000 | Lee et al. | |
| 6,110,179 A | 8/2000 | Flivik et al. | |
| 6,113,605 A | 9/2000 | Storer | |
| 6,132,469 A | 10/2000 | Schroeder | |
| 6,139,551 A | 10/2000 | Michelson et al. | |
| 6,146,423 A | 11/2000 | Cohen et al. | |
| 6,174,335 B1 | 1/2001 | Varieur et al. | |
| 6,187,012 B1 | 2/2001 | Masini | |
| 6,197,063 B1 | 3/2001 | Dews | |
| 6,264,299 B1 | 7/2001 | Noda | |
| 6,264,657 B1 | 7/2001 | Urbahns et al. | |
| 6,306,171 B1 | 10/2001 | Conzemius | |
| 6,322,564 B1 | 11/2001 | Surma | |
| 6,364,910 B1 | 4/2002 | Shultz et al. | |
| 6,368,271 B1 | 4/2002 | Sharratt | |
| 6,368,353 B1 | 4/2002 | Arcand | |
| 6,379,917 B1 | 4/2002 | Okun et al. | |
| 6,409,730 B1 | 6/2002 | Green et al. | |
| 6,508,840 B1 | 1/2003 | Rockwood, Jr. et al. | |
| 6,520,994 B2 | 2/2003 | Nogarin | |
| 6,537,278 B1 | 3/2003 | Johnson | |
| 6,626,913 B1 | 9/2003 | Mckinnon et al. | |
| 6,666,874 B2 | 12/2003 | Heitzmann et al. | |
| 6,736,851 B2 | 5/2004 | Maroney et al. | |
| 6,746,452 B2 | 6/2004 | Tuke et al. | |
| 6,783,549 B1 | 8/2004 | Stone et al. | |
| 6,786,684 B1 | 9/2004 | Ecker | |
| 6,797,006 B2 | 9/2004 | Hororek et al. | |
| 7,044,973 B2 | 5/2006 | Rockwood, Jr. et al. | |
| 7,097,663 B1 | 8/2006 | Nicol et al. | |
| 7,140,087 B1 | 11/2006 | Giltner | |
| 7,160,328 B2 | 1/2007 | Rockwood, Jr. et al. | |
| 7,169,184 B2 | 1/2007 | Dalla Pria | |
| 7,175,663 B1 | 2/2007 | Stone | |
| 7,179,084 B1 | 2/2007 | Kometas | |
| 7,189,036 B1 | 3/2007 | Watson | |
| 7,189,261 B2 | 3/2007 | Dews et al. | |
| 7,204,854 B2 | 4/2007 | Guederian et al. | |
| 7,208,222 B2 | 4/2007 | Rolfe et al. | |
| 7,344,565 B2 | 3/2008 | Seyer et al. | |
| 7,465,319 B2 | 12/2008 | Tornier | |
| 7,476,228 B2 | 1/2009 | Abou | |
| 7,476,253 B1 | 1/2009 | Craig et al. | |
| 7,585,327 B2 | 9/2009 | Winslow | |
| 7,615,080 B2 | 11/2009 | Ondrla | |
| 7,637,703 B2 | 12/2009 | Khangar et al. | |
| 7,648,530 B2 | 1/2010 | Habermeyer et al. | |
| 7,670,382 B2 | 3/2010 | Parrott et al. | |
| 7,678,150 B2 | 3/2010 | Tornier et al. | |
| 7,744,602 B2 | 6/2010 | Teeny et al. | |
| 7,758,650 B2 | 7/2010 | Dews et al. | |
| 7,887,544 B2 | 2/2011 | Tornier et al. | |
| 7,927,376 B2 | 4/2011 | Leisinger et al. | |
| D643,926 S | 8/2011 | Collins | |
| 8,021,370 B2 | 9/2011 | Fenton et al. | |
| 8,114,089 B2 | 2/2012 | Divoux et al. | |
| 8,162,947 B2 | 4/2012 | Dreyfuss | |
| 8,182,541 B2 | 5/2012 | Long et al. | |
| 8,187,282 B2 | 5/2012 | Tornier et al. | |
| 8,192,497 B2 | 6/2012 | Ondrla | |
| 8,202,275 B2 | 6/2012 | Wozencroft | |

(56) References Cited

U.S. PATENT DOCUMENTS

| | | | |
|---|---|---|---|
| 8,221,037 B2 | 7/2012 | Neitzell | |
| 8,231,682 B2 | 7/2012 | LaFosse | |
| 8,246,687 B2 | 8/2012 | Katrana et al. | |
| 8,262,667 B1 | 9/2012 | Silver et al. | |
| D668,331 S | 10/2012 | Ren et al. | |
| 8,277,512 B2 | 10/2012 | Parrott et al. | |
| 8,317,871 B2 | 11/2012 | Stone et al. | |
| 8,409,798 B2 | 4/2013 | Luy et al. | |
| 8,419,798 B2 | 4/2013 | Ondrla et al. | |
| D685,474 S | 7/2013 | Courtney | |
| 8,500,744 B2 | 8/2013 | Wozencroft et al. | |
| 8,506,638 B2 | 8/2013 | Vanasse et al. | |
| 8,512,410 B2 | 8/2013 | Metcalfe et al. | |
| D691,710 S | 10/2013 | White | |
| 8,545,506 B2 | 10/2013 | Long et al. | |
| 8,591,592 B2 | 11/2013 | Dreyfuss | |
| 8,641,773 B2 | 2/2014 | Bergin et al. | |
| 8,690,958 B2 | 4/2014 | Klawitter et al. | |
| 8,702,800 B2 | 4/2014 | Linares et al. | |
| 8,753,402 B2 | 6/2014 | Winslow et al. | |
| 8,840,671 B2 | 9/2014 | Ambacher | |
| 8,845,742 B2 | 9/2014 | Kusogullari et al. | |
| 8,864,834 B2 | 10/2014 | Boileau et al. | |
| 8,870,962 B2 | 10/2014 | Roche et al. | |
| 8,876,908 B2 | 11/2014 | Katrana et al. | |
| 8,882,845 B2 | 11/2014 | Wirth et al. | |
| D745,678 S | 12/2015 | Courtney et al. | |
| 9,233,003 B2 | 1/2016 | Roche et al. | |
| 9,241,804 B2 | 1/2016 | Iannotti | |
| 9,289,218 B2 | 3/2016 | Courtney, Jr. et al. | |
| 9,326,865 B2 | 5/2016 | Katrana et al. | |
| 9,498,345 B2 | 11/2016 | Brukhead, Jr. et al. | |
| 9,510,951 B2 | 12/2016 | Bachmaier | |
| 9,610,165 B2 | 4/2017 | Poncet et al. | |
| 9,956,083 B2 | 5/2018 | Humphrey | |
| D831,218 S | 10/2018 | Da Costa | |
| D840,539 S | 2/2019 | Courtney et al. | |
| 10,456,264 B2 | 10/2019 | Hodorek | |
| 10,463,499 B2 | 11/2019 | Emerick et al. | |
| D875,936 S | 2/2020 | Martin | |
| 10,722,373 B2 | 7/2020 | Hodorek et al. | |
| 10,898,348 B2 | 1/2021 | Vivanz et al. | |
| 10,945,862 B2 | 3/2021 | Roby et al. | |
| 11,076,962 B2 | 8/2021 | Kemp et al. | |
| D938,034 S | 12/2021 | Knox et al. | |
| 11,229,524 B2 | 1/2022 | Sperling | |
| D951,449 S | 5/2022 | Knox et al. | |
| D952,143 S | 5/2022 | Conklin | |
| D983,372 S | 4/2023 | Knox et al. | |
| D985,125 S | 5/2023 | Knox et al. | |
| 2001/0034533 A1 | 10/2001 | Michelson | |
| 2001/0047210 A1 | 11/2001 | Wolf | |
| 2001/0049561 A1 | 12/2001 | Dews et al. | |
| 2002/0116007 A1 | 8/2002 | Lewis | |
| 2002/0156534 A1 | 10/2002 | Grusin et al. | |
| 2003/0004573 A1 | 1/2003 | Bagby | |
| 2003/0028253 A1 | 2/2003 | Stone et al. | |
| 2003/0031521 A1* | 2/2003 | Haughton | B23B 51/04 |
| | | | 408/203.5 |
| 2003/0114933 A1 | 6/2003 | Bouttens et al. | |
| 2003/0125810 A1 | 7/2003 | Sullivan et al. | |
| 2004/0010262 A1 | 1/2004 | Parkinson et al. | |
| 2004/0010319 A1 | 1/2004 | McTighe et al. | |
| 2004/0049270 A1 | 3/2004 | Gewirtz | |
| 2004/0186586 A1 | 9/2004 | Seyer et al. | |
| 2004/0193276 A1 | 9/2004 | Maroney et al. | |
| 2004/0193277 A1 | 9/2004 | Long et al. | |
| 2004/0193278 A1 | 9/2004 | Maroney et al. | |
| 2004/0220674 A1 | 11/2004 | Pria | |
| 2004/0225367 A1 | 11/2004 | Glien et al. | |
| 2004/0243136 A1 | 12/2004 | Gupta et al. | |
| 2004/0254646 A1 | 12/2004 | Stone et al. | |
| 2005/0107882 A1 | 5/2005 | Stone et al. | |
| 2005/0112397 A1 | 5/2005 | Rolfe et al. | |
| 2005/0203539 A1 | 9/2005 | Grimm et al. | |
| 2005/0209597 A1 | 9/2005 | Long et al. | |
| 2005/0261775 A1 | 11/2005 | Baum et al. | |
| 2005/0267478 A1 | 12/2005 | Corradi et al. | |
| 2006/0004378 A1 | 1/2006 | Raines | |
| 2006/0009852 A1 | 1/2006 | Winslow et al. | |
| 2006/0020344 A1 | 1/2006 | Shultz et al. | |
| 2006/0064173 A1 | 3/2006 | Guederian | |
| 2006/0079963 A1 | 4/2006 | Hansen | |
| 2006/0089656 A1 | 4/2006 | Allard et al. | |
| 2006/0142866 A1 | 6/2006 | Baratz et al. | |
| 2006/0195105 A1 | 8/2006 | Teeny et al. | |
| 2006/0200165 A1 | 9/2006 | Tulkis | |
| 2006/0200249 A1 | 9/2006 | Beguin et al. | |
| 2007/0010825 A1 | 1/2007 | Leisinger et al. | |
| 2007/0055380 A1 | 3/2007 | Berelsman et al. | |
| 2007/0100458 A1 | 5/2007 | Dalla Pria | |
| 2007/0123890 A1 | 5/2007 | Way et al. | |
| 2007/0123893 A1 | 5/2007 | O'Donoghue | |
| 2007/0123909 A1 | 5/2007 | Rupp et al. | |
| 2007/0156246 A1 | 7/2007 | Meswania et al. | |
| 2007/0162038 A1 | 7/2007 | Tuke | |
| 2007/0162141 A1 | 7/2007 | Dews et al. | |
| 2007/0173945 A1 | 7/2007 | Wiley et al. | |
| 2007/0212179 A1 | 9/2007 | Khangar et al. | |
| 2007/0219562 A1 | 9/2007 | Slone et al. | |
| 2007/0219638 A1 | 9/2007 | Jones et al. | |
| 2007/0225817 A1 | 9/2007 | Reubell et al. | |
| 2007/0233132 A1 | 10/2007 | Valla | |
| 2007/0288096 A1 | 12/2007 | Surma | |
| 2008/0004711 A1 | 1/2008 | Li et al. | |
| 2008/0021564 A1 | 1/2008 | Gunther | |
| 2008/0077146 A1 | 3/2008 | Pernsteiner et al. | |
| 2008/0172061 A1 | 7/2008 | Ragbir | |
| 2008/0177393 A1 | 7/2008 | Grant et al. | |
| 2008/0195111 A1 | 8/2008 | Anderson | |
| 2008/0221576 A1 | 9/2008 | Keller | |
| 2008/0228281 A1 | 9/2008 | Forrer et al. | |
| 2008/0249577 A1 | 10/2008 | Dreyfuss | |
| 2009/0099662 A1 | 4/2009 | Splieth et al. | |
| 2009/0171462 A1 | 7/2009 | Poncet et al. | |
| 2009/0192621 A1 | 7/2009 | Winslow et al. | |
| 2009/0281630 A1 | 11/2009 | Delince et al. | |
| 2009/0306782 A1 | 12/2009 | Schwyzer | |
| 2010/0042214 A1 | 2/2010 | Nebosky et al. | |
| 2010/0087927 A1 | 4/2010 | Roche et al. | |
| 2010/0114326 A1 | 5/2010 | Winslow et al. | |
| 2010/0121331 A1 | 5/2010 | Sharp et al. | |
| 2010/0191340 A1 | 7/2010 | Dreyfuss | |
| 2010/0268238 A1 | 10/2010 | Sikora et al. | |
| 2010/0274359 A1 | 10/2010 | Brunnarius et al. | |
| 2010/0274360 A1 | 10/2010 | Gunther | |
| 2010/0278601 A1 | 11/2010 | Beynon | |
| 2010/0331902 A1 | 12/2010 | Biegun | |
| 2011/0082587 A1 | 4/2011 | Ziaei et al. | |
| 2011/0153023 A1 | 6/2011 | Deffenbaugh et al. | |
| 2011/0224673 A1 | 9/2011 | Smith | |
| 2011/0276144 A1 | 11/2011 | Wirth et al. | |
| 2011/0313533 A1 | 12/2011 | Gunther | |
| 2012/0022664 A1 | 1/2012 | Vandermeulen et al. | |
| 2012/0071985 A1 | 3/2012 | Hodorek et al. | |
| 2012/0083769 A1 | 4/2012 | Burgi et al. | |
| 2012/0109321 A1 | 5/2012 | Stone et al. | |
| 2012/0184964 A1 | 7/2012 | Hudak, Jr. | |
| 2012/0221111 A1 | 8/2012 | Burkhead, Jr. et al. | |
| 2012/0221112 A1 | 8/2012 | Lappin | |
| 2012/0232562 A1 | 9/2012 | Mani et al. | |
| 2012/0265315 A1 | 10/2012 | Kusogullari et al. | |
| 2012/0265319 A1 | 10/2012 | Prybyla et al. | |
| 2012/0277880 A1 | 11/2012 | Winslow et al. | |
| 2012/0290099 A1 | 11/2012 | Gibson et al. | |
| 2012/0296435 A1 | 11/2012 | Ambacher | |
| 2013/0018382 A1 | 1/2013 | Jones et al. | |
| 2013/0018476 A1 | 1/2013 | Katrana et al. | |
| 2013/0123929 A1 | 5/2013 | McDaniel et al. | |
| 2013/0123930 A1 | 5/2013 | Burt | |
| 2013/0150972 A1 | 6/2013 | Iannotti et al. | |
| 2013/0173006 A1 | 7/2013 | Duport | |
| 2013/0178943 A1 | 7/2013 | Duport | |
| 2013/0211539 A1 | 8/2013 | McDaniel et al. | |

(56) References Cited

U.S. PATENT DOCUMENTS

| | | |
|---|---|---|
| 2013/0261626 A1 | 10/2013 | Chavarria et al. |
| 2013/0261629 A1 | 10/2013 | Anthony et al. |
| 2013/0261630 A1 | 10/2013 | Courtney, Jr. et al. |
| 2013/0261754 A1 | 10/2013 | Anthony et al. |
| 2013/0261755 A1 | 10/2013 | Anthony et al. |
| 2013/0282129 A1 | 10/2013 | Phipps |
| 2013/0331849 A1 | 12/2013 | Splieth et al. |
| 2014/0012272 A1 | 1/2014 | Leisinger |
| 2014/0012380 A1 | 1/2014 | Laurence et al. |
| 2014/0058523 A1 | 2/2014 | Walch et al. |
| 2014/0074246 A1 | 3/2014 | Huebner et al. |
| 2014/0081270 A1 | 3/2014 | Klotz et al. |
| 2014/0107792 A1 | 4/2014 | Hopkins et al. |
| 2014/0156012 A1 | 6/2014 | Winslow |
| 2014/0236304 A1 | 8/2014 | Hodorek et al. |
| 2014/0257499 A1 | 9/2014 | Winslow et al. |
| 2014/0288657 A1 | 9/2014 | Lederman et al. |
| 2014/0296988 A1 | 10/2014 | Winslow et al. |
| 2014/0330390 A1 | 11/2014 | Liu et al. |
| 2014/0358239 A1 | 12/2014 | Katrana et al. |
| 2014/0358240 A1 | 12/2014 | Katrana et al. |
| 2014/0379089 A1 | 12/2014 | Bachmaier |
| 2015/0039093 A1 | 2/2015 | McTighe et al. |
| 2015/0134066 A1 | 5/2015 | Bachmaier |
| 2015/0250601 A1 | 9/2015 | Humphrey |
| 2015/0265411 A1 | 9/2015 | Deransart et al. |
| 2015/0289984 A1 | 10/2015 | Budge |
| 2015/0297354 A1 | 10/2015 | Walch et al. |
| 2015/0328015 A1 | 11/2015 | Olson et al. |
| 2016/0051367 A1 | 2/2016 | Gervasi et al. |
| 2016/0059403 A1 | 3/2016 | Mugnier |
| 2016/0157911 A1 | 6/2016 | Courtney, Jr. et al. |
| 2016/0206445 A1 | 7/2016 | Gheevarughese et al. |
| 2016/0324648 A1 | 11/2016 | Hodorek et al. |
| 2016/0331551 A1 | 11/2016 | Slade et al. |
| 2016/0374815 A1 | 12/2016 | Siccardi et al. |
| 2017/0056187 A1 | 3/2017 | Humphrey et al. |
| 2017/0105843 A1 | 4/2017 | Britton et al. |
| 2017/0112634 A1 | 4/2017 | Gunn et al. |
| 2017/0273800 A1 | 9/2017 | Emerick et al. |
| 2017/0304063 A1 | 10/2017 | Hatzidakis et al. |
| 2017/0367714 A1 | 12/2017 | Mcculloch et al. |
| 2017/0367836 A1 | 12/2017 | Cardon et al. |
| 2018/0028249 A1 | 2/2018 | Jaumard |
| 2018/0092757 A1 | 4/2018 | Behzadi et al. |
| 2018/0103967 A1 | 4/2018 | Rouyer et al. |
| 2018/0161176 A1 | 6/2018 | Vivanz et al. |
| 2018/0193168 A1 | 7/2018 | Termanini et al. |
| 2018/0200067 A1 | 7/2018 | Axelson et al. |
| 2018/0206859 A1 | 7/2018 | Pendleton et al. |
| 2018/0280152 A1 | 10/2018 | Mutchler et al. |
| 2019/0159906 A1 | 5/2019 | Knox et al. |
| 2019/0175354 A1 | 6/2019 | Knox et al. |
| 2019/0231544 A1 | 8/2019 | Boileau et al. |
| 2019/0231558 A1 | 8/2019 | Beck et al. |
| 2019/0336307 A1 | 11/2019 | Sungu et al. |
| 2019/0374349 A1 | 12/2019 | Müller |
| 2020/0000573 A1 | 1/2020 | Whittaker et al. |
| 2020/0121474 A1 | 4/2020 | Pendleton et al. |
| 2020/0188123 A1 | 6/2020 | Hodorek et al. |
| 2020/0188125 A1 | 6/2020 | Hodorek et al. |
| 2020/0214845 A1 | 7/2020 | Knox et al. |
| 2020/0214853 A1 | 7/2020 | Sweitzer |
| 2020/0222205 A1 | 7/2020 | Gosik-Wolfe et al. |
| 2021/0030565 A1 | 2/2021 | Dun et al. |
| 2021/0045895 A1 | 2/2021 | Sapio et al. |
| 2021/0212840 A1 | 7/2021 | Sweitzer et al. |
| 2021/0212841 A1 | 7/2021 | Sweitzer et al. |
| 2021/0228362 A1 | 7/2021 | Whitwell et al. |
| 2021/0228370 A1 | 7/2021 | Ek et al. |
| 2021/0228372 A1 | 7/2021 | Knox et al. |
| 2021/0244487 A1 | 8/2021 | Beck |
| 2021/0251643 A1 | 8/2021 | Stump |
| 2021/0290411 A1 | 9/2021 | Gosik-Wolfe |
| 2021/0315713 A1 | 10/2021 | Keach et al. |
| 2021/0330476 A1 | 10/2021 | Alden |
| 2021/0338456 A1 | 11/2021 | Wolfe et al. |
| 2021/0386558 A1 | 12/2021 | Alden |
| 2021/0393414 A1 | 12/2021 | Robicheaux et al. |
| 2022/0023053 A1 | 1/2022 | Kim et al. |
| 2022/0023071 A1 | 1/2022 | Sweitzer |
| 2022/0031464 A1 | 2/2022 | Knox et al. |
| 2022/0039811 A1 | 2/2022 | Bahk |
| 2022/0104835 A1 | 4/2022 | Blaser et al. |
| 2022/0117756 A1 | 4/2022 | Blaser et al. |
| 2022/0125591 A1 | 4/2022 | Rivera, Jr. |
| 2022/0151794 A1 | 5/2022 | Fattori et al. |
| 2022/0233322 A1 | 7/2022 | Knox et al. |
| 2023/0145300 A1 | 5/2023 | Paterson et al. |
| 2023/0149177 A1 | 5/2023 | Hodorek et al. |

FOREIGN PATENT DOCUMENTS

| | | |
|---|---|---|
| DE | 4220217 | 12/1993 |
| DE | 10233204 | 1/2004 |
| DE | 102004042502 | 3/2006 |
| EP | 0 274 094 | 8/1990 |
| EP | 1 413 265 | 4/2004 |
| EP | 0 959 822 | 5/2004 |
| EP | 1 125 565 | 12/2004 |
| EP | 1 518 519 | 3/2005 |
| EP | 1 004 283 | 5/2005 |
| EP | 1 639 967 | 3/2006 |
| EP | 1 762 191 | 3/2007 |
| EP | 1 952 788 | 8/2008 |
| EP | 1 867 303 | 9/2010 |
| EP | 1 977 720 | 1/2011 |
| EP | 1 550 420 | 2/2012 |
| EP | 2 261 303 | 11/2012 |
| EP | 1 706 074 | 12/2012 |
| EP | 2 564 814 | 3/2013 |
| EP | 2 567 676 | 3/2013 |
| EP | 2 574 313 | 4/2013 |
| EP | 2586387 A1 | 5/2013 |
| EP | 2 616 013 | 7/2013 |
| EP | 2 474 288 | 9/2013 |
| EP | 2 663 263 | 5/2014 |
| EP | 2 502 605 | 8/2014 |
| EP | 2 800 541 | 11/2014 |
| EP | 2 815 726 | 8/2015 |
| EP | 2 353 549 | 6/2016 |
| EP | 3117801 | 1/2017 |
| EP | 2965720 B1 | 7/2017 |
| FR | 2 674 122 | 9/1992 |
| FR | 2980685 B1 | 10/2013 |
| FR | 2997290 B1 | 11/2015 |
| JP | 2002506361 A | 2/2002 |
| JP | 2005511243 A | 4/2005 |
| JP | 2006523106 A | 10/2006 |
| JP | 2009523578 A | 6/2009 |
| JP | 2015532863 A | 11/2015 |
| JP | 2016528956 A | 9/2016 |
| JP | 2019506281 A | 3/2019 |
| WO | WO 01/67988 | 9/2001 |
| WO | WO 02/17822 | 3/2002 |
| WO | WO 2008/011078 | 1/2008 |
| WO | WO 2008/146124 | 12/2008 |
| WO | WO 2011/081797 | 7/2011 |
| WO | WO 2012/035263 | 3/2012 |
| WO | WO 2012/130524 | 10/2012 |
| WO | WO 2013/009407 | 1/2013 |
| WO | WO 2013/064569 | 5/2013 |
| WO | WO 2013/148229 | 10/2013 |
| WO | WO 2014/005644 | 1/2014 |
| WO | WO 2014/058314 | 4/2014 |
| WO | WO 2015/112307 | 7/2015 |
| WO | 2016094739 A1 | 6/2016 |
| WO | WO2016094739 | 6/2016 |
| WO | WO 2017/165090 | 9/2017 |
| WO | WO 2017/184792 | 10/2017 |
| WO | WO 2018/022227 | 2/2018 |
| WO | WO2019/060780 | 3/2019 |
| WO | 2019133905 A1 | 7/2019 |

(56) References Cited

FOREIGN PATENT DOCUMENTS

OTHER PUBLICATIONS

Boileau, et al., "The Three-Dimensional Geometry of the Proximal Humerus: Implications for Surgical Technique and Prosthetic Design," J Bone Joint Surg, Sep. 1997, vol. 79-B, Issue 5, pp. 857-865.

Routman, et al., "Reverse Shoulder Arthroplasty Prosthesis Design Classification System," Bulletin of the Hospital for Joint Diseases, 2015, vol. 73 (Suppl 1), pp. S5-S14.

French Search report issued in Application No. FR1157282, dated Feb. 27, 2012, in 1 page.

Non-Final Office Action issued in connection with U.S. Appl. No. 17/250,964, filed Jul. 26, 2021, 27 pages.

Final Rejection issued in connection with U.S. Appl. No. 16/249,720, filed Aug. 20, 2021, 40 pages.

Final Rejection issued in connection with U.S. Appl. No. 16/580,367, filed Aug. 24, 2021, 9 pages.

Non-Final Office Action issued in connection with U.S. Appl. No. 16/519,937, filed Aug. 17, 2021, 21 pages.

Final Office Action issued in connection with U.S. Appl. No. 17/250,964, filed Sep. 9, 2021, 22 pages.

First Examination Report issued in connection with Australian Patent Application No. 2020360410, Nov. 24, 2022, 5 pages.

First Office Action issued in connection with Japanese Patent Application No. 2022-520122, Apr. 18, 2023, 4 pages.

Med Gadget, "Tornier Announces First Implant in U.S. Trial of Its Simpliciti Stemless Shoulder Joint Replacement System", first available Aug. 5, 2011. (https://Avwww.medgadget.com/2011/08/tornier-announces-first-implant-in-u-s-trial-of-its-simpliciti-stemless-shoulder-joint-replacement-system.html) (Year: 2011).

Wright Media, "Tornier Aequalis Reversed FX", first available May 19, 2016. (https://Avww.wrightemedia.com/ProductFiles/Files/PDFs/ CAW-1146_EN_LR_LE.pdf) (Year: 2016).

Wright Media, "Aequalis Ascend Flex", first available Jul. 30, 2019. (https://Avww.wrightemedia.com/ProductFiles/Files/PDFs/AP-010187_EN_LR_LE.pdf) (Year: 2019).

Arthrex, "Univers Revers Shoulder System", first available Apr. 24, 2019. (https://Awww.arthrex.com/resources/surgical-technique-guide/ qkv6M00_50qt2QFBx1PKnA/univers-revers-shoulder-system) (Year: 2019).

Notice of Allowance issued in connection with U.S. Appl. No. 18/150,254, filed Mar. 20, 2024, 11 pages.

Non-Final Office Action issued in connection with U.S. Appl. No. 16/648,128, dated Mar. 28, 2022, 43 pages.

Non-Final Office Action issued in connection with U.S. Appl. No. 17/250,964, filed Feb. 24, 2022, 12 pages.

First Office Action issued in connection with Japanese Patent Application No. 2019-555151, Feb. 21, 2022, 5 pages.

Final Office Action issued in connection with Japanese Patent Application No. 2022-520122, Sep. 26, 2023, 3 pages.

Non-Final Office Action issued in connection with U.S. Appl. No. 17/281,683, filed Oct. 6, 2023, 7 pages.

Office Action issued in connection with Japanese Patent Application No. 2021-518159, May 24, 2022, 5 pages.

Third Examination Report issued in connection with Australian Patent Application No. 2019355854, May 10, 2022, 4 pages.

First Examination Report issued in connection with Australian Patent Application No. 2021250994, Jun. 2, 2022, 5 pages.

Non-Final Office Action issued in connection with U.S. Appl. No. 17/717,253, filed Jun. 29, 2022, 56 pages.

Office Action issued in connection with Japanese Patent Application No. 2021-518174, May 24, 2022, 7 pages.

Non-Final Office Action issued in connection with U.S. Appl. No. 17/634,623, 11 pages, Apr. 30, 2024.

Non-Final Office Action issued in connection with U.S. Appl. No. 17/664,435, filed Jun. 20, 2024, 16 pages.

First Office Action issued in connection with Chinese Patent Application No. 202080069828.6, Aug. 15, 2024, 9 pages.

Extended European Search Report issued in connection with European Patent Application No. 25156537.0, May 2, 2025, 9 pages.

First Office Action issued in connection with Japanese Patent Application No. 2024-016311, Jun. 3, 2025, 6 pages.

Non-Final Office Action issued in connection with U.S. Appl. No. 18/159,149, filed Aug. 22, 2025, 20 pages.

Decision of Rejection issued in connection with Japanese Patent Application No. 2024-016311, Oct. 14, 2025, 6 pages.

* cited by examiner

OSTEOTOME EXTRACTOR

CROSS-REFERENCE TO RELATED APPLICATION

This application claims the benefit of U.S. patent application Ser. No. 16/249,720, filed Jan. 16, 2019; Ser. No. 15/046,295, filed Feb. 17, 2016, now U.S. Pat. No. 10,213,243; and Ser. No. 13/553,610, filed Jul. 19, 2012, now U.S. Pat. No. 9,289,218; U.S. Provisional Patent Application No. 61/509,506 filed Jul. 19, 2011; and French Patent Application No. 20110057282, filed Aug. 10, 2011, which are all hereby incorporated by reference for all purposes as if fully set forth herein.

TECHNICAL FIELD

Embodiments of the present invention relate to a surgical tool for extraction of a prosthesis from a bony implantation site of that prosthesis as well as a surgical kit including such a surgical tool and such a prosthesis.

BACKGROUND

When a prosthesis has been implanted in a bone for a certain time, typically several years, it may prove necessary to remove the prosthesis for various reasons: for example, wear of the prosthesis, degeneration of the bony material of the prosthesis implantation site, trauma, and the like. The prosthesis removed is generally replaced by a revision prosthesis, the success and the implantation performance of which depend on the residual stock of bony material after removing the initial prosthesis. Consequently, surgeons aim to limit as much as possible any cutting of bony material necessary to free and extract the initial prosthesis.

With the arrival of prostheses with a porous surface or, more generally, adapted to have their surface colonized by the bone of the implantation site, extraction operations may prove particularly delicate. To this end, the surgeon generally employs osteotomes, the application of which may advantageously be guided to improve the precision of their action. Then, once the bonding interface between the prosthesis and the bony material has been cut in this way by these osteotomes, the surgeon uses another surgical tool to grasp and pull on the prosthesis in order to extract it.

SUMMARY

Embodiments of the present invention include a method for separating an implant from a bone, the method comprising: interfacing a tool with an implant including a flange, the flange including a proximal surface and a distal surface, the distal surface bearing on or facing the bone, the flange including an aperture defined through the flange; inserting an elongate element through the aperture from the proximal surface to the distal surface and into the bone; and partially separating a bonding interface between the implant and the bone using the elongate element.

Embodiments of the present invention include a surgical tool to extract an implant, the tool comprising: a main body; and a plurality of elongate elements extending distally from the main body along a direction that is substantially parallel to a longitudinal axis of the tool, each of the plurality of elongate elements including: a first edge extending in a longitudinal direction; a second edge opposite the first edge and extending in the longitudinal direction; and a distal edge extending between the first edge and the second edge;

wherein each of the plurality of elongate elements is configured to extend through a corresponding one of a plurality of apertures of the implant; and each of the plurality of elongate elements are configured to at least partially separate an interface between the implant and bony material at an implantation site of the implant.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
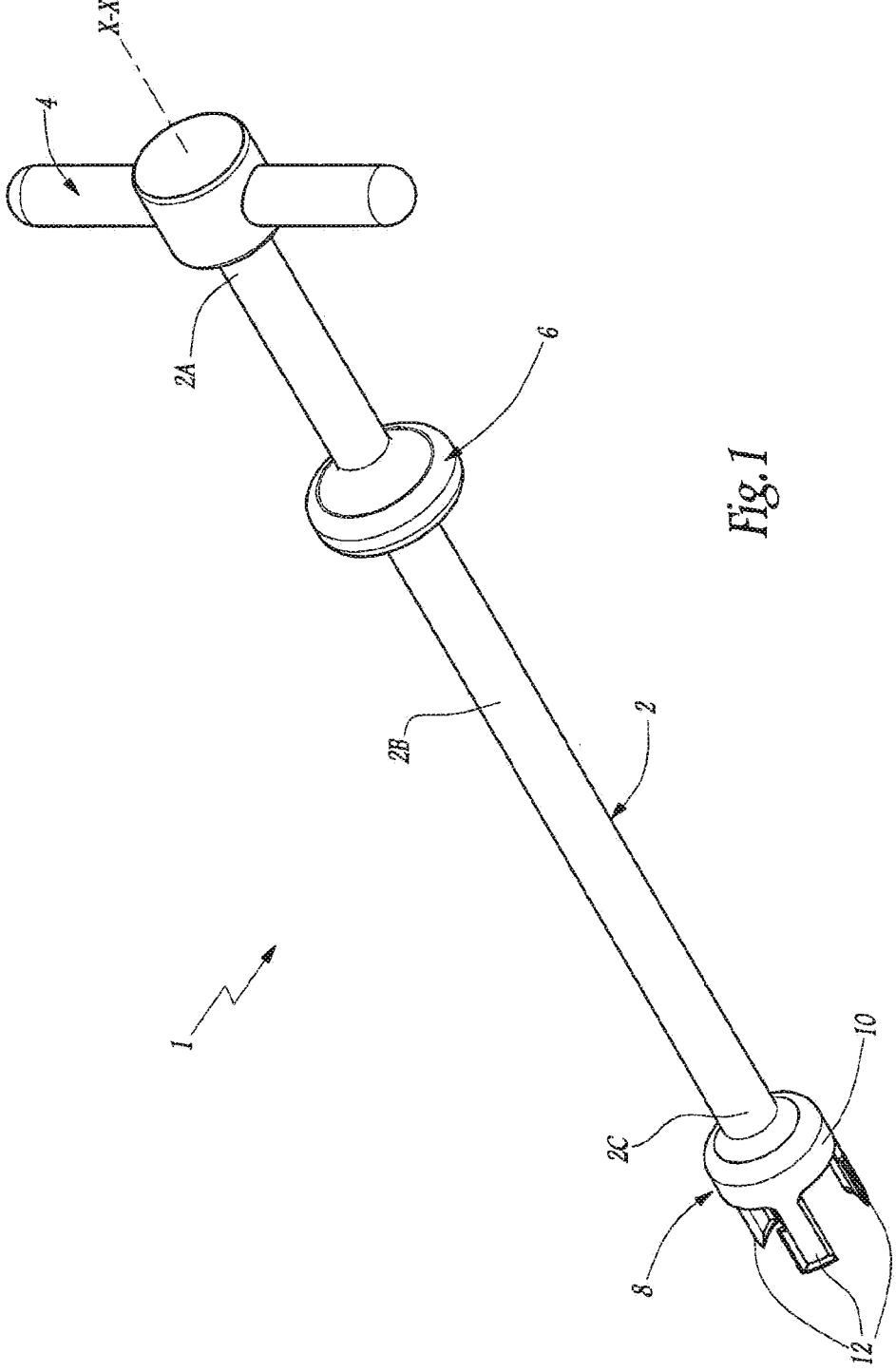
FIG. 1 is a perspective view of a surgical tool, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
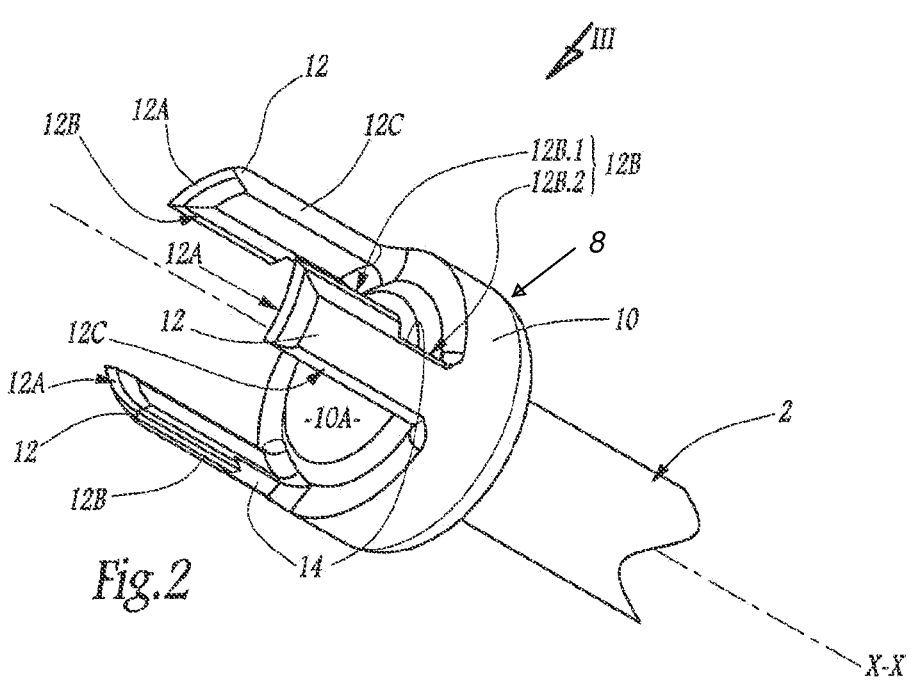
FIG. 2 is a perspective view as seen from a different angle and to a larger scale than FIG. 1 of a portion of the surgical tool from FIG. 1, according to embodiments of the present invention.
Figure 3:
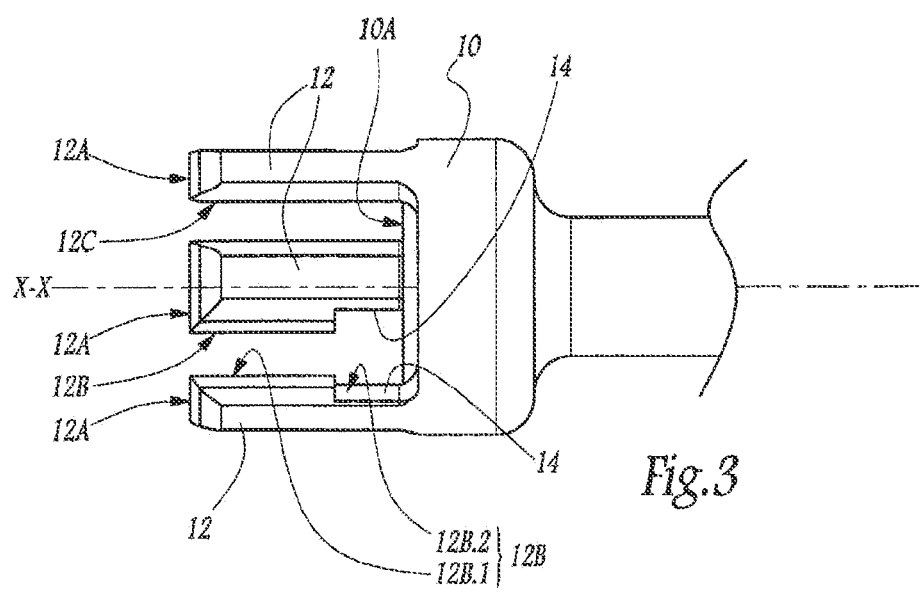
FIG. 3 is a view in elevation in the direction of the arrow III in FIG. 2, according to embodiments of the present invention.

In FIGS. 1 to 3 there is represented a surgical tool 1 for extracting a prosthesis from a bony implantation site of that prosthesis. As seen clearly in FIG. 1, this surgical tool 1 has an elongate overall shape, centered on a longitudinal axis X-X which, in use, extends in a direction which, at the proximal end, faces toward the surgeon and, at the distal end faces toward the bony implantation site of the prosthesis to be extracted.

The surgical tool 1 includes a shaft 2 that is centered on and extends lengthwise along the axis X-X and which includes a cylindrical rod of circular section. At its proximal end 2A, the shaft 2 is provided with a fixed handle 4 arranged transversely to the axis X-X, in order to facilitate driving, for example manual driving, of the surgical tool 1 by a user. This handle 4 may be formed in the shape of a "T". In its main part 2B, the shaft 2 is fixedly provided with a shoulder 6 projecting radially from the rest of the shaft 2. The shoulder 6 may be comprised of a disc centered on the axis X-X. Alternatively, shoulder 6 may be a cylindrical handle, a roughened surface, one or more indentations, one or more protrusions, or any other shape which permits shoulder 6 to receive a traction force and transmit the traction force to the shaft, according to embodiments of the present invention.

At its end 2C, the shaft 2 includes a fixed head 8 that cooperates mechanically with a prosthesis to be extracted. As illustrated in FIGS. 1 to 3, this head 8 includes a main body 10 that is centered on the axis X-X and is generally disc-shaped. According to one embodiment, the head 8 includes three elements 12, which may be separate and identical. In other embodiments, the head 8 may include one, two, three, four, five, six or more elements 12. In still other embodiments, the elements 12 may not be identical and one or more element 12 may have different lengths, widths, thicknesses, curvatures, or other features as compared to one or more other elements 12. Each element 12 may have a shape that is elongate in the direction of the axis X-X and projects in the longitudinal axial direction from the distal face 10A of the main body 10 of the head 8. According to some embodiments of the present invention, each element 12 projects from a portion of the external periphery of the distal face 10A of the body 10. Each element 12 as a whole corresponds to a portion of a tubular wall centered on the axis X-X and projecting axially from the exterior periphery of the face 10A of the body 10, according to embodiments of the present invention. Elements 12 may be referred to as cutting elements, according to embodiments of the present invention.

According to one embodiment, the three elements 12 are distributed, for example, in a substantially regular manner (e.g. separated by substantially the same radial angles) around the axis X-X. In particular, these three elements 12 may correspond to respective portions of the same tubular wall. According to other embodiments, the two or more elements 2 are distributed in an irregular manner on the distal head 8, and are either not separated by similar radial angles, and/or are not situated about a perimeter of the distal head 8. For example, the elements 12 may be positioned on distal head 8 at different or staggered radial distances from the axis X-X, and may be positioned at different or staggered radial separations with respect to the axis X-X.

As shown in FIGS. 1 to 3, each element 12 has, axially opposite its proximal end connecting the rest of the element to the main body 10 of the head 8, a distal free edge 12A along which a cutting edge is formed in a direction peripheral to the axis X-X. Each element 12 may be delimited in a direction peripheral to the axis X-X by two opposite longitudinal free edges 12B and 12C. The longitudinal edge 12B, which is that oriented in the clockwise direction about the axis X-X when the head 8 is viewed from the proximal end 2A of the shaft 2, has, in its longitudinal direction, a distal end part 12B.1 along which a cutting edge is formed and a proximal end part 12B.2 in which a recessed notch 14 is delimited. Edge 12B may also be referred to as leading edge 12B, and edge 12C may be referred to as trailing edge 12C, according to embodiments of the present invention.

An example of use of the surgical tool 1 will now be described with reference to FIGS. 4 to 6.

Figure 4:
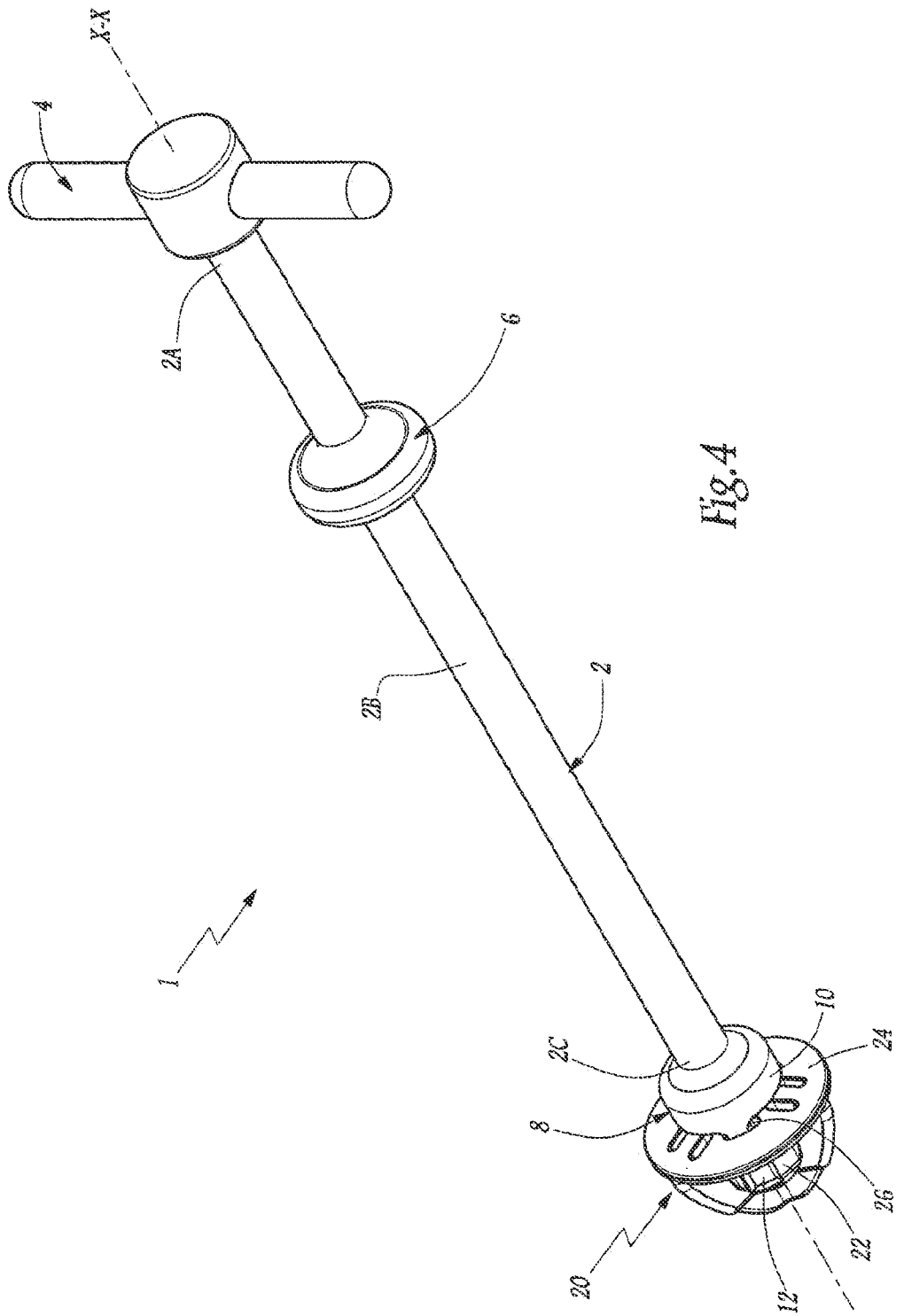
FIGS. 4 to 6 are views similar to FIGS. 1 to 3, respectively, showing the surgical tool from FIG. 1 associated with a prosthesis to be extracted with the aid of that surgical tool.
Figure 5:
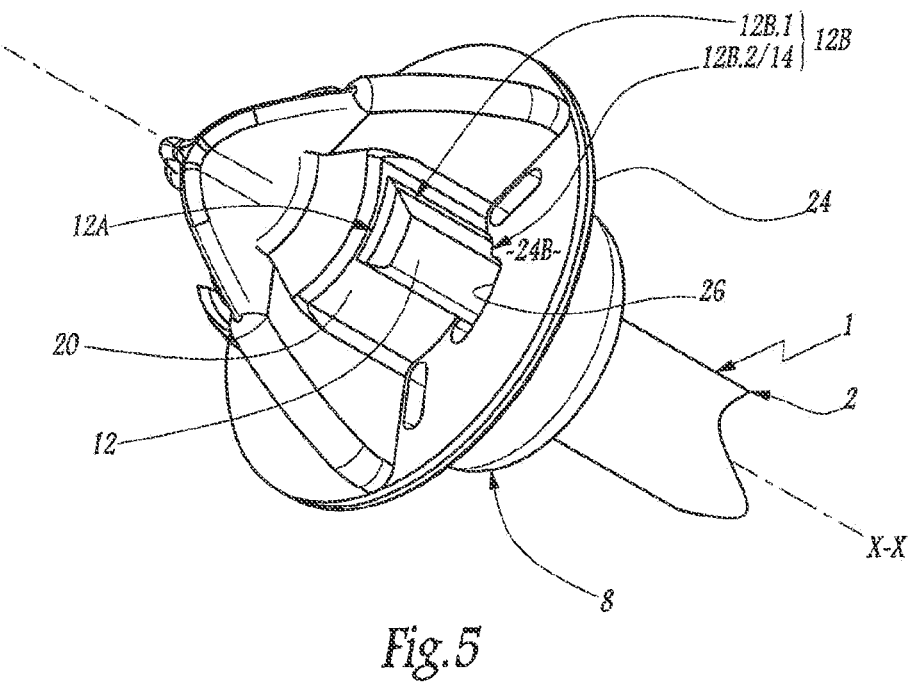
Figure 6:
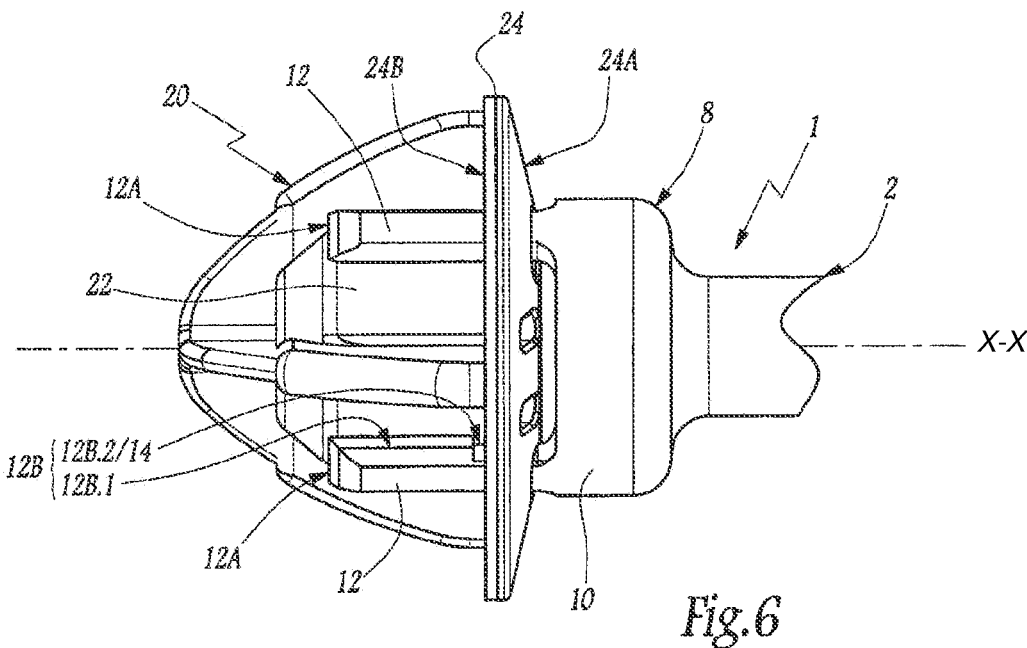

In these FIGS. 4 to 6, the head 8 of the surgical tool 1 cooperates with a prosthesis 20 to be extracted including an anchor body 22 anchored in the bony material of an implantation site of the prosthesis. This anchor body 22 is provided with a flange 24 which bears on the aforementioned implantation site. In some embodiments of the present invention, when the prosthesis 20 is in an implantation configuration, its body 22 is engaged depthwise in the bony material of the implantation site and its flange 24 remains outside or partially outside the bony material of the implantation site, bearing on the perimeter surface of the hole at the implantation site in which the body 22 is housed. Consequently, if a surgeon wishes to extract the prosthesis 20 from the aforementioned implantation site, the proximal face 24A of the flange 24 is directly accessible, whereas the distal face 24B of the flange 24 bears on the bony material of the implantation site. Given the context of the surgical intervention, the interface between the prosthesis 20, and more precisely the body 22 of that prosthesis, and the bony material of the implantation site proves resistant to extraction of the prosthesis 20 in the sense that, over time, a mechanical-biological bond has progressively formed at this interface between the prosthesis and the bony material. The strength of this bonding interface often proves particularly high in the situation in which the body 22 has a porous structure or, more generally, an exterior surface suitable for osteo-integration, as is generally the case when the prosthesis 20 is a prosthesis implanted without cement.

As used herein, the term "flange" is used in its broadest sense to refer to any structure or shape which has a proximal surface and a distal surface and is capable of contacting bone or being positioned on or near bone. For example, a flange may have a circular, square, rectangular, triangular, or other (regular or irregular) polygonal shaped cross-section along a dimension that is substantially perpendicular to the axis X-X, according to embodiments of the present invention. The perimeter of the flange may be smooth and/or continuously contoured, or may include straight segments, and/or may include a combination of both contoured and straight segments.

To extract the prosthesis 20, the surgeon grasps the shaft 2 of the surgical tool 1, notably by hand, and moves the head 8 toward the prosthesis 20, substantially aligning the axis X-X with a central geometrical axis of the prosthesis 20, in particular the central geometrical axis around which the flange 24 extends peripherally. The distal edge 12A of each element 12 of the head 8 can then be used to cut at least in part the bonding interface between the prosthesis 20 and the bony material of the implantation site. To this end, the flange 24 is provided with three through-slots 26 each of which connects the proximal face 24A and the distal face 24B of the flange 24 to each other. Each slot 26 has a cross section allowing, or even in some cases guiding, introduction into this slot of one of the elements 12, in a movement in translation oriented along the axis X-X and directed in the distal direction. In other words, each slot 26 may have a cross-sectional shape corresponding to a flat ring portion the width of which considered radially with respect to the axis X-X substantially corresponds to the radial thickness of each element 12 and the length of which, in a direction peripheral to the axis X-X, is substantially equal to the peripheral extent of the element 12, as illustrated in FIGS. 4 and 5, according to embodiments of the present invention.

The distal edge 12A of the elements 12 is introduced first into one of the slots 26 and projects therefrom, at the distal end, cutting the portion of the (bony) bonding interface between the prosthesis 20 and the bony material that it encounters on its trajectory in translation. The surgeon continues to drive the surgical tool 1 in translation distally along the axis X-X until the distal face 10A of the body 10 comes to bear against or in the immediate vicinity of the proximal face of the prosthesis 20, for example with the interior periphery of the proximal face 24A of the flange 24.

The surgeon then rotates the shaft 2 on itself about the axis X-X, in some cases using the handle 4 to increase the driving torque. In some cases, use of the handle 4 increases the driving torque tenfold. The head 8 is then driven in a similar rotary movement, causing the longitudinal edge 12B of each of its elements 12 to follow a circular trajectory, centered on the axis X-X, and, in the embodiment shown, in the clockwise direction. The distal end part 12B.1 of each of the edges 12B then cuts the part of the bonding interface between the body 22 of the prosthesis 20 and the bony material of the implantation site, situated on the circular trajectory of the edge 12B. At the same time, each notch 14 of the longitudinal edges 12 mechanically engages the flange 24 in the direction in which, given the rotary movement of the head 8 on itself about the axis X-X relative to the prosthesis 20, one of the peripheral ends of each slot 26 is introduced into the notch 14. This cases the slots 26 to become engaged, in a direction peripheral to the axis X-X, axially between the opposite axial edges of the notch 14. This rotation drive movement is continued by the surgeon so as to engage the flange 24 as far as to the bottom of the notches 14. The surgical tool 1 and the prosthesis 20 are then in the configuration of use represented in FIGS. 4 to 6.

Although notch 14 is shown as having an "L" shape, notch 14 may alternatively have other shapes, according to embodiments of the present invention. For example, the shape of notch 14 may be fully or partially curved, for example in a "U" shape, or may be segmented, for example in a "V" shape, according to embodiments of the present invention. Notch 14 may include any shape which is capable of accepting at least a portion of the inside edge of an aperture 26 upon rotation of the head 8, according to embodiments of the present invention. In one embodiment, the proximal end of notch 14 is delimited by a distal surface of the head 8 as shown in FIG. 3. In another embodiment, the proximal edge of notch 14 is located distally of the distal surface of the head 8. The shape of the proximal edge of the notch 14 may also take numerous forms, for example straight, curved, or a combination of straight and curved, according to embodiments of the present invention.

Although clockwise rotation is described, one of ordinary skill will appreciate, based on the present disclosure, that the tool 1 may alternatively be configured for counterclockwise rotation, according to embodiments of the present invention.

Upon engagement of the tool 1 with the prosthesis 20, the mechanical connection that the surgeon establishes between the head 8 of the surgical tool 1 and the flange 24 of the prosthesis 20 is a bayonet connection centered on the axis X-X, according to embodiments of the present invention.

The surgeon may exert a traction force along the axis X-X, directed in the proximal direction. The surgeon makes use of the shoulder 6, for example by mechanically engaging this shoulder 6 with an ad hoc tool (not shown), enabling the surgeon to increase (e.g. tenfold) the applied force to apply to the shaft 2 axial traction loads directed in the proximal direction. As the bonding interface between the prosthesis 20 and the bony material of the prosthesis implantation site has been cut in several areas, by the successive action of the distal edges 12A and the distal end parts 12B.1 of the longitudinal edges 12B of the elements 12, remaining uncut areas of this bonding interface are broken in a controlled manner as to their location, and easily, without the surgeon having to exert too great a traction force.

Thus the surgical tool 1 enables the prosthesis 20 to be extracted easily and quickly, it being noted that, due at least in part to its bayonet fixing, integrating partial cutting of the bonding interface between the prosthesis and the bony material of the implantation site, the surgeon does not need to use two separate instruments to turn and turn about to cut the aforementioned interface and then make the mechanical attachment to the prosthesis to be pulled.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A tool to extract an implant, the tool comprising:
a main body; and
a plurality of elongate elements extending distally from the main body along a longitudinal direction that is substantially parallel to a longitudinal axis of the tool, each of the plurality of elongate elements (i) including a leading edge extending in the longitudinal direction substantially parallel to the longitudinal axis of the tool, (ii) defining a recessed notch adjacent to the main body and including an edge that extends substantially orthogonally to the longitudinal axis, and (iii) including a distal cutting edge that is defined by a first tapered surface extending from an outside surface of the elongate element, a second tapered surface extending from an inside surface of the elongate element, and extending substantially orthogonally to the leading edge; wherein each of the plurality of elongate elements is configured to extend through a corresponding one of a plurality of slots of the implant; and
each recessed notch of the plurality of elongate elements is configured to engage a portion of the implant so as to at least partially separate an interface between the implant and bony material at an implantation site of the implant.

2. The tool of claim 1, wherein each of the plurality of elongate elements are configured to be guided by the corresponding one of the plurality of the slots of the implant.

3. The tool of claim 1, wherein each recessed notch is configured to lock into the corresponding one of the plurality of slots of the implant after each of the plurality of elongate elements has been extended through the corresponding one of the plurality of slots of the implant and upon rotation of the tool about the longitudinal axis.

4. A tool to extract an implant, the tool comprising:
a main body; and
a plurality of elongate elements extending distally from the main body along a direction that is substantially parallel to a longitudinal axis of the tool, each of the plurality of elongate elements including:
a first edge extending in a longitudinal direction substantially parallel to the longitudinal axis;
a second edge opposite the first edge and extending in the longitudinal direction substantially parallel to the longitudinal axis;
a recessed notch defined between the first edge and the main body and including an edge that extends substantially orthogonally to the longitudinal axis; and
a distal cutting edge that is defined by a first tapered surface extending from an outside surface of the elongate element and a second tapered surface extending from an inside surface of the elongate element and extending substantially orthogonally between the first edge and the second edge; wherein each of the plurality of elongate elements is configured to extend through a flange defining a corresponding one of a plurality of apertures of the implant; and
each of the plurality of elongate elements is configured to at least partially separate an interface between the implant and bony material at an implantation site of the implant when a portion of the flange that defines each aperture is located within a corresponding recessed notch.

5. The tool of claim 4, wherein the first edge is a cutting edge.

6. The tool of claim 4, wherein the first edge and the second edge of each of the plurality of elongate elements is entirely radially inward of an outer face of a respective elongate element.

7. The tool of claim 4, wherein each of the plurality of elongate elements extends along a portion of a tubular periphery centered on the longitudinal axis.

8. The tool of claim 4, wherein the plurality of elongate elements are spaced apart by substantially a same circumferential separation.

9. The tool of claim 4, wherein the plurality of elongate elements includes at least three elongate elements.

10. The tool of claim 4, wherein, in use, the distal cutting edge of each of the elongate elements is at a distal-most edge of the tool.

11. The tool of claim 4, wherein the tool further comprises a shaft extending along the longitudinal axis, a distal end of the shaft is affixed to the main body, a driving handle is affixed to a proximal end of the shaft, and a shoulder projecting radially from the shaft and positioned between the main body and the driving handle.

12. A tool to extract an implant, the tool comprising:

a main body; and a plurality of elongate elements extending distally from the main body along a direction that is substantially parallel to a longitudinal axis of the tool, each of the plurality of elongate elements including:

a first edge extending in a longitudinal direction substantially parallel to the longitudinal axis of the tool;

a second edge opposite the first edge and extending in the longitudinal direction substantially parallel to the longitudinal axis of the tool;

a recessed notch defined between the first edge and the main body and including an edge that extends substantially orthogonally to the longitudinal axis; and a distal cutting edge that is defined by a first tapered surface extending from an outside surface of the elongate element and a second tapered surface extending from an inside surface of the elongate element and extending substantially orthogonally between the first edge and the second edge; wherein each of the plurality of elongate elements is configured to extend through a flange defining a corresponding one of a plurality of apertures of the implant, each of the plurality of elongate elements is configured to at least partially separate an interface between the implant and bony material at an implantation site of the implant, and each of the plurality of elongate elements is configured to couple with the corresponding one of the plurality of apertures of the implant upon rotation of the tool about the longitudinal axis so that a portion of the flange that defines each aperture is located within a corresponding recessed notch.

* * * * *